(12) United States Patent
Buskirk et al.

(10) Patent No.: US 6,893,462 B2
(45) Date of Patent: May 17, 2005

(54) SOFT AND CALCIFIED TISSUE IMPLANTS

(75) Inventors: Dayna Buskirk, Alachua, FL (US); Chris Seid, Alachua, FL (US); John F. Wironen, Alachua, FL (US); James M. Gross, Alachua, FL (US); Gina Scurti, Alachua, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 144 days.

(21) Appl. No.: 09/942,537

(22) Filed: Aug. 29, 2001

(65) Prior Publication Data

US 2002/0072806 A1 Jun. 13, 2002

Related U.S. Application Data

(63) Continuation of application No. 09/782,594, filed on Feb. 12, 2001, and a continuation of application No. 09/750,192, filed on Dec. 28, 2000, and a continuation of application No. 09/481,319, filed on Jan. 11, 2000.
(60) Provisional application No. 60/296,530, filed on Jun. 6, 2001, and provisional application No. 60/181,622, filed on Feb. 10, 2000.

(51) Int. Cl.[7] .................................................. A61F 2/08
(52) U.S. Cl. .................................................. 623/13.17
(58) Field of Search ............................. 623/13.11–13.2, 623/17.11–17.18; 606/72, 73

(56) References Cited

U.S. PATENT DOCUMENTS

| | | | | |
|---|---|---|---|---|
| 4,744,793 A | * | 5/1988 | Parr et al. | 623/13.14 |
| 4,828,562 A | * | 5/1989 | Kenna | 623/13.13 |
| 5,171,326 A | | 12/1992 | Ducheyne et al. | 623/66 |
| 5,769,899 A | * | 6/1998 | Schwartz et al. | 606/77 |
| 5,782,832 A | * | 7/1998 | Larsen et al. | 606/61 |
| 5,961,520 A | * | 10/1999 | Beck et al. | 606/72 |
| 6,019,792 A | * | 2/2000 | Cauthen | 623/17.14 |
| 6,106,556 A | * | 8/2000 | Demopulos et al. | 623/13.16 |
| 6,129,762 A | * | 10/2000 | Li | 623/13.11 |
| 6,179,874 B1 | * | 1/2001 | Cauthen | 623/17.14 |
| 6,190,412 B1 | | 2/2001 | Lee et al. | 623/16.11 |
| 6,579,295 B1 | * | 6/2003 | Supinski | 606/72 |

* cited by examiner

*Primary Examiner*—Alvin Stewart
(74) *Attorney, Agent, or Firm*—McAndrews, Held & Malloy; Donald J. Pochopien

(57) ABSTRACT

Disclosed herein is processed dermis graft for use in orthopedic surgical procedures. Specifically exemplified herein is a processed dermis graft comprising one or more bone blocks having a groove cut into the surface thereof, wherein said groove is sufficient to accommodate a fixation screw. Also disclosed is a method of processing dermis that results in a dermis derived implant suitable to replace a tendon or ligament in a recipient in need thereof. Other compositions and applications of a dermis derived implant, and methods of manufacture and use, are disclosed.

29 Claims, 8 Drawing Sheets

End View

SOFT AND CALCIFIED TISSUE IMPLANTS

CROSS REFERENCE TO RELATED APPLICATION

This application is a continuation of U.S. application Ser. No. 60/296,530, filed on Jun. 6, 2001, and a continuation of U.S. application Ser. No. 09/481,319, filed on Jan. 11, 2000, and a continuation of U.S. application Ser. No. 09/750,192, filed Dec. 28, 2000, and a continuation of U.S. application Ser. No. 09/782,594, filed Feb. 12, 2001, which itself is a continuation of U.S. application Ser. No. 60/181,622 Feb. 10, 2000. The benefit of priority under 35 USC 119, 120 is claimed for the foregoing applications, and are also incorporated by reference.

BACKGROUND OF THE INVENTION

Orthopedic medicine is increasingly becoming aware of the vast potential and advantages of using grafts made from allograft bone to treat and repair spinal and common joint injuries, such as Anterior Cruciate Ligament (ACL) or Posterior Cruciate Ligament (PCL) tears. In the case of injuries involves surgically reconnecting the torn portions of a damaged ligament. However, this technique is often not possible, especially when the damage to the ligament is extensive. The recent utilization of bone/tendon grafts has dramatically improved the results of joint repair in cases of severe trauma. Even in cases of extensive damage to the joint ligaments, orthopedic surgeons have been able to achieve 100 percent range of motion and stability using donor bone/tendon grafts.

Despite these realized advantages, there have been some difficulties encountered with utilizing bone/tendon grafts. For example, surgical procedures involving transplantation and fixation of these grafts can be tedious and lengthy. Currently, bone/tendon/bone grafts must be specifically shaped for the recipient during surgery, which can require thirty minutes to over an hour of time. Further, surgeons must establish a means of attaching the graft, which also takes up valuable surgery time.

Another difficulty associated with using allograft implants, such as bone/tendon grafts, is that there is only a limited supply of source tissue. As a result, patients often have to settle for inferior surgical procedures simply based on the lack of availability of tissue. Accordingly, there is a need in the art for the development of implants that implement unrealized sources of tissue.

SUMMARY OF THE INVENTION

One aspect of the subject invention concerns methods of production and compositions for a novel dermis-derived graft (DDG) that facilitates an easier and more efficient surgery for reconstructing ligaments in a joint. While the embodiments herein exemplify the use of dermis tissue, it is understood that other tissue types can be adapted for use in accord with the teachings herein. Specifically, other soft tissues can be used such as ligament, tendon, muscle, dura, pericardium, fascia, and peritoneum, as well as demineralized bone. Tissues can be derived from allogenic, autogenic, or xenogenic sources. Alternatively synthetic materials may be used alone or in combination with natural materials. In one embodiment, the subject invention pertains to a DDG that comprises a section of processed dermis that is rolled to a cylindrical shape, and two bone blocks positioned at opposite ends of the rolled dermis, wherein the bone blocks are pre-shaped for uniform and consistent alignment into a recipient bone.

In a specific aspect, the subject invention pertains to a dermis derived bone-ended graft useful in orthopedic surgery comprising one or more bone blocks, and processed dermis attached to said one or more bone blocks; wherein said one or more bone blocks is cut to provide a groove sufficient to accommodate a fixation screw. Alternatively, the subject invention pertains to a dermis derived bone-ended graft useful in orthopedic surgery comprising one or more bone blocks and processed dermis attached to said one or more bone blocks, wherein said one or more bone blocks is pre-shaped into a dowel.

Another aspect of the invention regards a process for calcification of all or part of a dermis implant. Comparative data are provided that show the relative performance of processed dermis implants in laboratory rats, in which dermis implants had been calcified prior to implantation.

Another aspect of the invention regards the calcification of all or part of a tissue selected from: soft tissue; pericardium; fascia; woven soft tissue (as from skeletal muscle); urinary bladder membrane (UBM); and SIS.

Another aspect of the invention is the use of processed dermis as a replacement or as auxiliary support for the Anterior Longitudinal Ligament (ALL), and for use as a Spinal Tension Band (STB) or other type of tension band. For the ALL and STB, the dermis is formed into a shape that spans the anterior of at least two vertebrae (for an ALL support structure) or at least four vertebrae (for an STB), and the ends are affixed to a part of the vertebrae. The preferred attachment points for an STB are at the spinous processes of the adjacent vertebrae. This minimizes movement of (and thereby reduces degradation of) of the vertebrae adjacent to the vertebrae that are being fused. Such adjacent vertebrae are known to undergo excessive wear due to the lack of motion of the adjacent fused vertebrae. The ALL- and STB-type DDGs provide tensioning to help prevent excessive back bending due to the partial or total functional loss of the ALL owing to surgery or traumatic injury. As disclosed herein, the ends of dermis for such use preferably are calcified, and starting materials other than dermis may be used for such applications.

Preferably, the dermis is processed according to a method that preserves the dermis basement membrane. A process known to accomplish this is the subject of U.S. Patent Application Ser. No. 60/296,530, which is incorporated by reference. In yet another aspect, the subject invention pertains to a method of conducting orthopedic surgery on an animal comprising obtaining a dermis derived bone-ended graft, said graft comprising processed dermis having two ends, and one or more bone blocks attached to said processed dermis, wherein at least one of said one or more bone blocks has a groove suitable for accommodating a fixation screw.

An alternative aspect of the invention pertains to an implant comprising a bone block and processed dermis, wherein the bone block comprises a groove for accommodating a fixation screw.

These and other advantageous aspects of the subject invention are described in further detail below.

DETAILED DESCRIPTION OF THE DRAWINGS

FIGS. 1B–E represent an implant comprising a specific assembled bone block.

FIG. 2 is a diagram depicting implant embodiments in accord with the teachings herein.

Figure 3A:
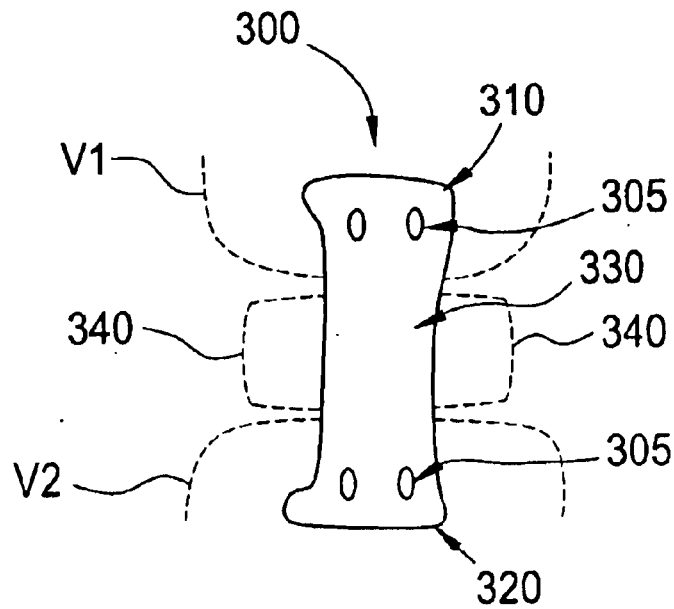
Figure 3B:
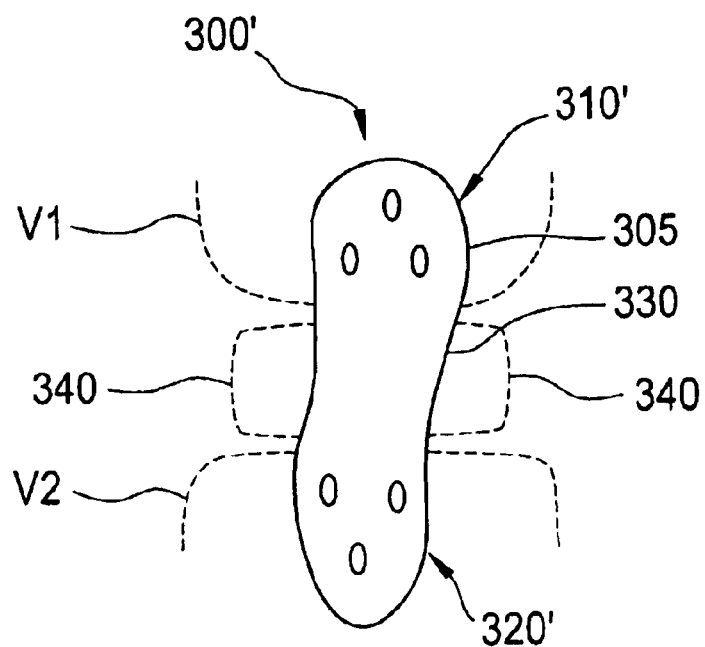

FIG. 3 depicts a first embodiment FIG. 3A and depicts a second embodiment FIG. 3B of an anterior longitudinal replacement for limiting motion between adjacent vertebrae to be fused.

Figure 4:
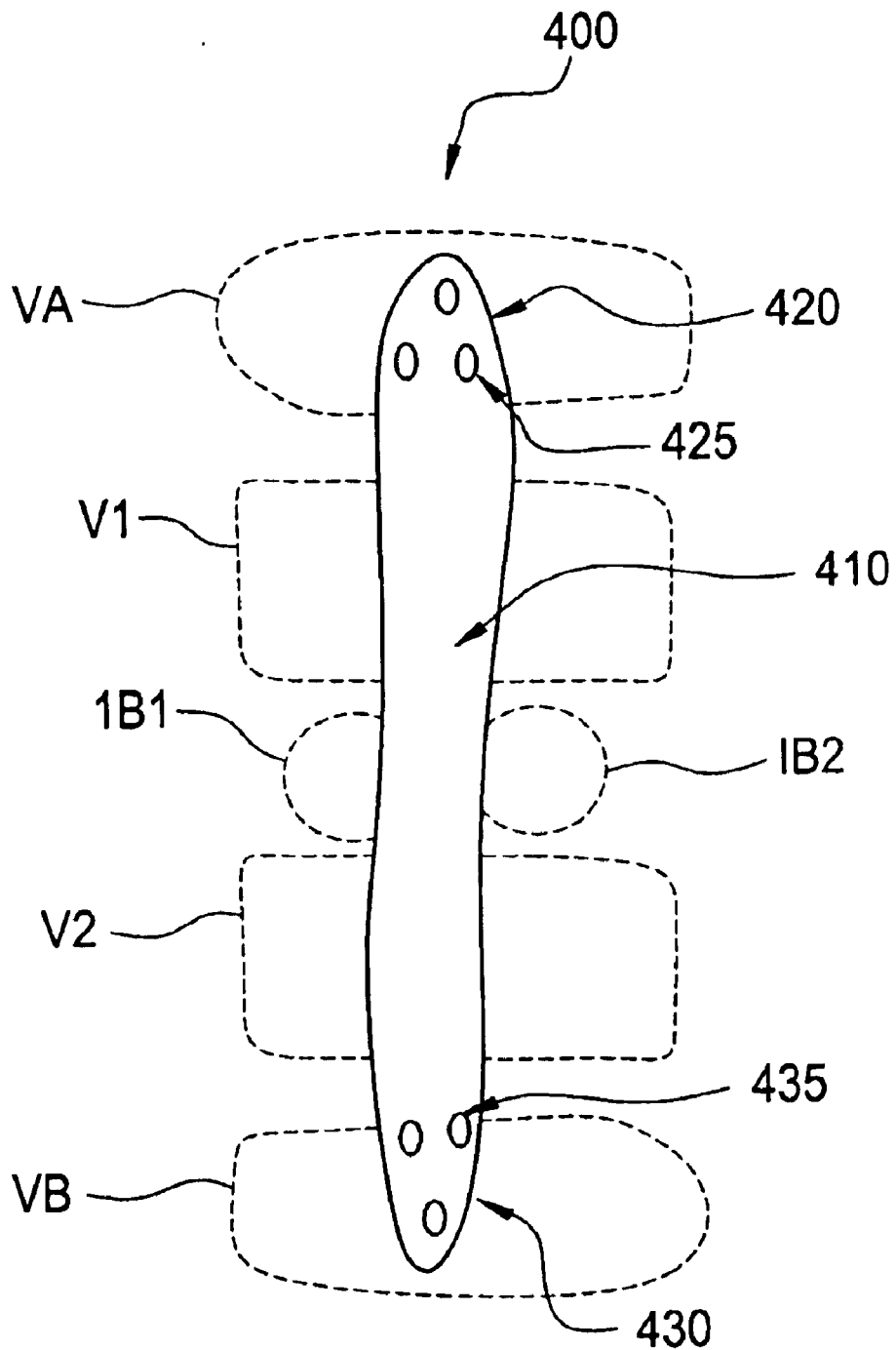

FIG. 4 depicts a band for limiting the motion and reducing the degradation of vertebrae juxtaposed to vertebrae undergoing spinal fusion (i.e., as a spinal tension band) or for being affixed to any other anatomical structures to minimize motion of such structures in relation to each other.

FIG. 5 shows plan and perspective views of a bone fixation plug that compresses the soft tissue graft component of the implant as the plug is being tightened into a hole.

DETAILED DISCLOSURE OF THE INVENTION

The present invention uses processed dermis as a material for implants which can be used as replacement or reinforcing tendons, ligaments, and the like. Particular features of the methods and the products of the present invention provide for a dermis-based implant that remodels into a 'new' replacement tendon or ligament. The present invention also discloses a process for the calcification of dermis and other tissues, including soft tissue, pericardium, fascia, woven soft tissue (as from skeletal muscle), urinary bladder membrane (UBM), and SIS. These collectively are referred to as "implant material," and when processed, as "processed implant material." The bone that is used in this application, for instance to comprise bone blocks, may be selected from cortical, cancellous, cortico-cancellous, or demineralized bone, obtained from human or xenograft sources. Optionally, synthetic material may be incorporated in combination with such bone. Also, bone blocks may be comprised of two or more segments assembled together in a assembled allograft implant. The construction and use of assembled allograft implants is disclosed more fully in U.S. patent application Ser. No. 09/782,594, which is incorporated by reference.

Other features provide for implants fabricated for specific applications, such as to supplement or replace the anterior longitudinal ligament of the spine. Methods of initial preparation and production of dermis implants, and of specific production for use as ALL- and STB-type implants are also disclosed.

I. Preparation of Dermis Derived Graft Material

For the purposes of this disclosure, the term "tendon", unless otherwise indicated, is taken to mean flexible fibrous connective tissue that attaches muscle to bone. In the context of bone/tendon/bone grafts, tendon can refer to the fibrous connective tissue that connects the patella to the femur and tibia. The term "ligament" is taken to mean the more general term of any fibrous structure connecting one body part to another, and more particularly to flexible, fibrous connective tissue that connects bone to bone or holds organs in place. Also, the term "processed dermis" is taken to mean dermis that has been processed by the initial processing described herein, or another method of decellularizing dermis, and by the secondary process described herein, in which the initially processed dermis is formed into an implant. A dermis derived graft (DDG) is synonymous with a dermis derived implant, and these terms are defined to indicate a graft or implant substantially comprised of processed dermis.

The term "processed dermis" as used herein is intended in a broad sense and refers to fibrous connective tissue for use in grafts derived from dermis of a donor, or from dermis cultured in vitro. The preferred initial processing is that described in U.S. Patent Application Ser. No. 60/296,530, which is incorporated by reference. The initial processing provides a decellularized dermis sample that retains the structural functionality of the basement membrane. This results in superior structural and functional properties of the final dermis derived implant.

Basic steps of a preferred initial processing method are summarized as follows:

1. Contacting the donor dermis with a viral inactivating agent that includes benzalkonium chloride; and
2. Contacting the dermis with one or more decellularizing agents, for instance about 0.5 percent Tween 20 and about 0.5 percent hydrogen peroxide.

Additional possible steps include contacting the dermis with calcium hydroxide (to aid in virus inactivation), with a chelating agent, for instance EDTA, sonicating the dermis during such treatments, and drying the dermis, such as by freeze-drying.

Preferably, a method in accordance with U.S. Patent Application No. 60/296,530 is used for initial preparation of the dermis. For example, dermis is selected that is at least 0.7 mm thick, and is free of epidermis, muscle, fat, hair, scars, moles, debris and tattoos. The dermis is cut to a desired size, and is soaked in 1 M NaCl. Thereafter the dermis is soaked in a 1% solution of benzalkonium chloride at 2–6 degrees Centigrade for 1–24 hours to reduce microbial load. Then the dermis is immersed in a solution of 1% Tween 20 and 0.5% hydrogen peroxide, and is sonicated for approximately 15 minutes at room temperature, stirring at least once per minute. Preferably, microbial load is further reduced by soaking in saturated calcium hydroxide solution while sonicating for approximately 15 minutes. The dermis is rinsed in purified water to remove the calcium hydroxide.

Thereafter the calcium in the dermis is chelated with EDTA by soaking in a 0.1% EDTA solution for about 15 minutes, and stirring or sonicating. After two rinses to remove the EDTA, the dermis pH is neutralized with buffer. Then purified water rinses remove the buffer. Drying is begun with soaking in 70% isopropanol, and is completed with freeze-drying. In general, the volume of solution to dermis is at least tenfold. This or similar initial processing provides dermis ready for further specific processing of the present invention.

In one specific, detailed initial processing procedure, the following steps are used:

1. Wash dermis obtained from donor(s) in sodium monophosphate buffer, pH = 7.0, and transfer to a bottle containing a one percent BZK (benzalkonium chloride) solution. Store by freezing.
2. Thaw dermis and transfer to a 1 Molar NaCl solution and incubate overnight at room temperature. This separates the epidermis.
3. Remove the epidermis and rinse dermis in sterile deionized water. Cut into desired sizes as needed.
4. Place dermis into a 0.5% hydrogen peroxide solution and sonicate for 15 minutes at room temperature. All dermis must be covered with the solution during this step.
5. Transfer the dermis to a solution (in excess relative to the dermis sample) of any of the following: 0.5% Tween-20; 0.5% sodium dodecyl sulfate; 1.0% Triton X-100. Then sonicate for 15 minutes at room temperature.
6. Transfer dermis to an excess solution (relative to dermis sample) of saturated, filtered CaOH. Then sonicate for 15 minutes at room temperature.
7. Rinse twice with de-ionized water, then transfer to an approximately 0.1% EDTA solution, let soak for 15 minutes, then rinse twice with deionized water.

-continued

8. Rinse dermis sample(s) in an excess solution of sodium monophosphate buffer (pH = 7.0) three times, for five minutes each time.
9. Rinse dermis sample(s) in sterile deionized water.
10. Transfer dermis sample(s) to an excess of 70% isopropyl alcohol for 15 minutes to dehydrate the dermis (do not sonicate).
11. Package dermis, or cut to size (if not already cut), and package for lyophilization.
12. Lyophilize the sample(s).
13. Treat dermis with a low dose of gamma radiation.

After initial processing, in certain applications the dermis is further processed to form, as described in section III, implant structures suitable for use as a tendon or ligament. Alternately, the dermis is used for other types of implants, including those referred to in section IV below.

The major component of the processed dermis is collagen. A cross linking step may be added in the initial processing, or in the subsequent processing where the implant is being formed or shaped (such as in section II), to cross link collagen molecules. Cross linking approaches have been described in a previous application for a moldable bone paste, U.S. application Ser. No. 09/750,192, which is incorporated by reference, and is described here for the present application.

Typical chemical cross-linking agents used in accord with this invention include those that contain bifunctional or multifunctional reactive groups, and which react with collagen of the processed dermis. By reacting with multiple functional groups on the same or different collagen molecules, the chemical cross-linking agent increases the mechanical strength of the implant.

The cross-linking step of the subject embodiment involves treatment of the dermis to a treatment sufficient to effectuate chemical linkages between adjacent molecules. Typically, such linkages are between adjacent collagen molecules exposed on the surface of the dermis. Crosslinking conditions include an appropriate pH and temperature, and times ranging from minutes to days, depending upon the level of crosslinking desired, and the activity of the chemical crosslinking agent. Preferably, the implant is then washed to remove all leachable traces of the chemical.

Suitable chemical cross linking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as heterobifunctional crosslinking agents; hexamethylene diisocyante; sugars, including glucose, will also cross link collagen.

It is known that certain chemical cross-linking agents, e.g., glutaraldehyde, have a propensity to exceed desired calcification of cross-linked, implanted biomaterials. In order to control this calcification, certain agents can be added into the composition of the subject embodiment, such as dimethyl sulfoxide (DMSO), surfactants, diphosphonates, aminooleic acid, and metallic ions, for example ions of iron and aluminum. The concentrations of these calcification-tempering agents can be determined by routine experimentation by those skilled in the art.

When enzymatic cross-linking treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery*, 79-a (2), 185–193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen cross links between surface-exposed collagen. Such methods include using energy in the form of ultraviolet light, microwave energy and the like. Another method utilizing the application of energy is a process known as dye-mediated photo-oxidation in which a chemical dye under the action of visible light is used to cross link surface-exposed collagen.

Another method for the formation of chemical linkages is by dehydrothermal treatment which uses combined heat and the slow removal of water, preferably under vacuum, to achieve crosslinking of collagen in the processed dermis. The process involves chemically combining a hydroxy group from a functional group of one collagen molecule and a hydrogen ion from a functional group of another collagen molecule reacting to form water which is then removed resulting in the formation of a bond between the collagen molecules.

II. Preparation of Calcified Dermis Derived Implant

It has been learned that the ends, other sections of, or an entire piece of the processed dermis, may be calcified by the following process. By modifying the twelve-step method shown above, such that the contacting with calcium hydroxide solution is followed immediately by the phosphate buffer solution, calcium is deposited onto (or precipitates onto) the dermis. Approaches to calcifying the dermis sample include contacting with the phosphate buffer slowly, as by changing out the solution in which the dermis section is held, or rapidly, as by moving the dermis section from a vessel containing the calcium hydroxide to a vessel containing phosphate buffer. The preferred pH of the phosphate buffer is in the range of 6.8 to 7.2 pH units. While not being bound to a particular theory, the change in pH is believed to cause a precipitation of calcium onto the processed dermis. The deposited calcium adds rigidity to the section. It has been observed that calcification will not occur appreciably if the EDTA solution is used between the calcium hydroxide step and the phosphate buffer step. The following evaluation illustrates one use of calcified dermis prepared according to this invention.

Evaluation of Initially Prepared Dermis in Animal Model

Samples of dermis were prepared using the twelve-step method described in section I, varying the type and amount of detergent agent, as shown in the table of results.

Thereafter, the dermis so prepared was implanted and evaluated as described below.

A. Sample Preparation for Implantation

1.) Lyophilized dermis was cut (aseptically) into approximately 1×1 cm implants, weighed before hydration (pre-implantation dry weight), and rehydrated with sterile saline containing antibiotics.
2.) Samples were implanted (4 per rat) into Athymic nude rat model following SOP# with modification: only one suture was used to hold the implant in place.
3.) Implants were recovered at 3, 6, and 12 week post-implantation (2 week samples per donor/per treatment/per time point—total of 6 for each treatment/time point) 1–2 were kept for historical analysis and 4–5 were removed, lyophilized to determine dry-weight post-implantation (to determine percent loss of tissue after in vivo exposure).

B. Animal Surgeries

1.) Surgeries were performed as follows: Animals were anesthetized via intramuscular injection (thigh or gluteus muscle) of ketamine (100 mg/k) and Xylazine (15 mg/kg). Sterile technique was used and surgery was performed in a class 100 hood. Alcohol and providone iodine were applied to the abdomen of the animal. An incision was made parallel to the midline of the abdomen from just below the tip of the sternum to just above the navel. The skin is dissected away from the underlying muscle on either side of the abdomen. The muscle is isolated and a 0.5×0.5 cm area of fascia was scored from the muscle until the muscle bled, one are in each quadrant of the abdomen. A 1×1 cm piece of dermis was sutured to the muscle over the area that was previously scored, with two corners of the dermis sutured in to place with non-absorbable 3-O prolyene suture. The skin was closed with wound clips in a continuous line. Providone iodine is reapplied to the wound and the animal is returned to its' cage. according to (Rat Assay Osteoinductivity Surgery) with the following exceptions:
2.) At 3, 6, and 12 weeks, animals were sacrificed according to a humane procedure.
3.) The skin was shaved on the stomach using a disposable razor or hair clippers.
4.) The muscle flap with the overlying skin was removed.
5.) The entire muscle flap was photographed for macroscopic observation.
6.) Implant material was removed (6 per time point for each test sample), and placed in labeled sterile petri dishes for drying. If implants were difficult to remove, the entire muscle flap was removed and the implant was carefully excised using scalpels in the lab. Before dissection, each implant site was photographed for documentation purposes.
7.) 3 implants of each sample at each time point was prepared for histological processing. (H&E staining)

C. Results and Discussion

| Implant | Group | Dry Implant Weight | Dry Explant Weight | % Change |
|---|---|---|---|---|
| 1Fa | 40 SDS | .0225 | .0542 | +140.9% |
| 1Ed | | .0218 | .0469 | +115.1% |
| 1Bd | | .0236 | .0259 | +9.7% |
| 1Gd | 40 Triton | .0121 | .0352 | +190.9% |
| 1He | | .0126 | .0404 | +220.6% |
| 2Ad | | .0086 | .0271 | +215.1% |
| 1Db | 40 Tween | .0073 | .0231 | +216.4% |
| 2Fe | | .0091 | .0309 | +239.6% |
| 1Fe | | .0073 | .0289 | +295.9% |
| 2Eb | 41 SDS | .0148 | .0370 | +150% |
| 1Eb | | .0107 | .0342 | +219.6% |
| 1Cb | | .0104 | .0342 | +228.8% |
| 2Ee | 41 Triton | .0068 | .0272 | +300% |
| 1Gb | | .0080 | .0282 | +243.9% |
| 2Be | | .0077 | .0304 | +294.8% |
| 2Da | 41 Tween | .0075 | .0239 | +218.7% |
| 2Ca | | .0071 | .0241 | +239.4% |
| 2Aa | | .0079 | .0282 | +257% |
| 2Fb | 42 SDS | .0062 | .0207 | +233.9% |

-continued

| Implant | Group | Dry Implant Weight | Dry Explant Weight | % Change |
|---|---|---|---|---|
| 1Db | | .0073 | .0231 | +216.4% |
| 1Ee | | .0079 | .0242 | +206.3% |
| 1Bd | 42 Triton | .0096 | .0585 | +509.4% |
| 1Ce | | .0111 | .0332 | +199.1% |
| 1Aa | | .0099 | .0322 | +225.3% |
| 2Fa | 42 Tween | .0129 | .0446 | +245.7% |
| 1Fb | | .0093 | .0290 | +211.8% |
| 1Dd | | .0155 | .0555 | +258.1% |

Explants appeared to have calcified during the first four-week period to a low degree. X-Ray analysis confirmed the presence of calcified matrix. This is postulated to be due to neutralization of the CaOH treatment with buffer which resulted in the precipitation of calcium phosphate on the tissue. When calcification of the dermis is not desired, the dermis can be thoroughly washed with sterile water and EDTA prior to neutralization with buffer.

These results show an increased level of bone deposition that is believed related to the initial levels of calcification described in this section. In vivo the implants became much less pliable compared to implants processed in a standard, non-calcifying manner. The inventors believe that in some applications, some forms of calcified, processed dermis implants could form bone. This is based on the fact that both demineralized bone (which forms bone as an implant) and acellular dermis are comprised of primarily Type I collagen In addition, growth and other factors, as are known in the art and administered to suit the purpose of the particular application, are added to the implant. For example, prior to assembly or after assembly, the graft materials are soaked, infused, impregnated, coated or otherwise treated with bone morphogenetic proteins (BMP's), antibiotics, growth factors (including angiogenic growth factors), nucleic acids, peptides, and the like.

It is noted that all or part of other tissue samples, whether allograft, xenograft or autograft, may be calcified in accordance with the present invention. Examples of such tissues include: soft tissue; pericardium; fascia; woven soft tissue (as from skeletal muscle); urinary bladder membrane (UBM); and SIS. Accordingly, where the term DDG is used in regard to calcification, it is appreciated that these tissue types may be substituted for the dermis tissue. Variations in the duration of a particular step, and other modifications of the above described processes, may be required to optimize the process for each such tissue. However, such modifications are within the scope of reasonable experimentation having the above process as guidance.

III. Production of Dermis-Derived and Other Types of Tendon/Ligament-Type Implants Dermis processed as described above, or as processed by other methods, can be fabricated into an implant that substitutes for or replaces a tendon or ligament in a recipient in need thereof. The dermis derived implant may be used as a scaffold for tendon and ligament regeneration, a locus for remodeling that is superior to other implant choices (e.g., demineralized ligament, urinary bladder matrix, small intestine submucosa). While not being bound to a particular theory, this is believed due to the presence of a collagen structure that is less labile to enzymatic degradation than other implant choices, and to the presence of the basement membrane. However, it is understood that other materials may be utilized in accord with the teachings herein, including but not limited to, demineralized bone (partially or fully), ligaments, tendons, peritoneum, urinary bladder matrix, dura mater, and muscle, from allograft and xenograft sources.

The following embodiments of implants and their production are meant to be illustrative, and not limiting. It is noted that for the following embodiments, the processed dermis is a material suited for remodeling by the recipient's body into a 'new' tendon or ligament.

Thus, one aspect of the present invention is processing dermis for specific use as a tendon implant. For example, a section of dermis initially processed by the method described in section I is reconstituted by soaking in a 5% gelatin solution for two minutes. The section is rolled around a wooden swab to establish a desired thickness and mass for the intended application. One end, approximately ½ inch, of the rolled dermis is immersed in a saturated calcium hydroxide solution, and this is sonicated for 10 minutes. The dermis is soaked in 50 mM phosphate buffer for 10 minutes, and soaked in acetone for 30 minutes for initial drying. Drying is continued with placement in a drying oven set to approximately 60 degrees Centigrade for two hours.

Following the above procedure, in one trial it was observed that the layers of the dermis, upon subsequent reconstitution, slightly separated in some places.

In a subsequent trial, the dermis was soaked in gelatin as above, rolled around the swab mandrel and secured with suture material. Then this was wrapped in a paper towel and rolled under pressure. This was frozen, and then freeze-dried. The step of soaking in acetone was excluded. The dermis so processed was more difficult to separate compared to the first trial's samples. It was determined in animal trials that the implant only needs to hold together during surgery because proper fixation at the ends will ensure that the implant functions.

Typical embodiments of dermis-derived tendons and ligaments comprise a main intermediate section of processed dermis and two ends for attachment of the implant to desired body parts of a recipient. In one embodiment, one or more soft tissue screws are used to attach each end to a desired body part. In another embodiment, one or both ends are fixed in a substance (for instance, alpha-BSM, hydroxyapatite, calcium sulfate) which hardens the end(s) and allows the use of a hard tissue interference screw for attachment to the recipient's body part. This is described in section II. Alternately, as described below, the ends are attached to pieces of bone that are suited for subsequent attachment to the recipient's body part.

In addition to the above basic steps, the dermis may be cross linked, such as by the methods and agents described in section I. Alternately, or in addition, an appropriate biocompatible adhesive may be added to attach the outer flap to the immediately underlying layer. Alternately, or in addition, the dermis is held together and on the swab (or other mandrel-like device) with string, twine, suture material, or other wrapping. Pressure is applied as needed to help hold the rolled layers together. Layering the dermis provides additional strength, and cross linking the layers further adds to the strength.

In addition, growth and other factors, as are known in the art and administered to suit the purpose of the particular application, are added to the implant. For example, prior to assembly or after assembly, the graft materials are soaked, infused, impregnated, coated or otherwise treated with antibiotics, growth factors (including angiogenic growth factors), nucleic acids, peptides, and the like.

Figure 1A:
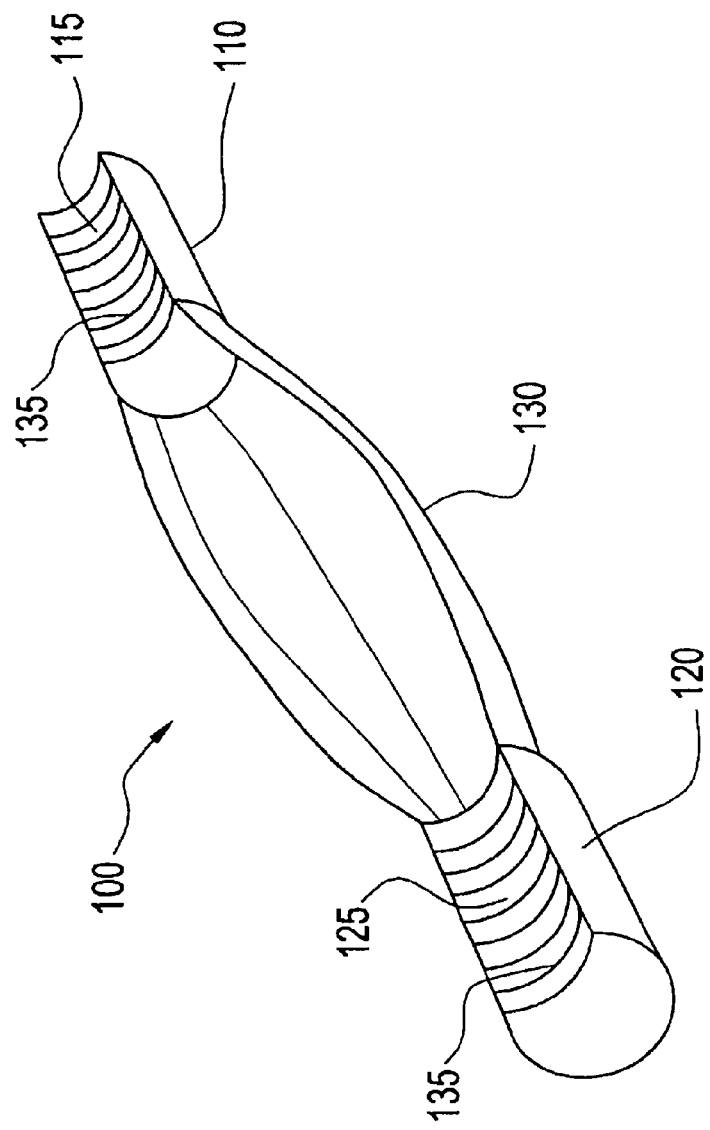
FIG. 1A shows a bone-tendon-bone type implant.

Regarding the use of pieces of bones at one or more ends of the processed dermis, referring to FIG. 1A, there is shown an embodiment directed to a DDG 100 comprising a first bone block 110 and a second bone block 120 interconnected by processed dermis 130, in which the bone blocks have been pre-shaped into dowels.

To facilitate placement of a fixation screw, dowels are preferably machined down the length of the bone block to form radius cuts 115, 125. The radius cuts 115, 125 aid in the attachment of the graft to recipient bone because they provide a groove to position a fixation screw, which results in increased surface area at the contact between the bone block and the screw. The radius cuts 115, 125 provide the additional advantage of increasing the pull out loads of the bone block, as well as filling of dead space in tunnel.

Fixation methods known in the art can be used in accord with the principles of the subject invention, which include, but are not limited to, staples, buttons, screw and washer, interference screws, and self-taping screws. In a preferred embodiment, fixation is accomplished by interference screws and/or self-tapping screws. In an even more preferred embodiment, the radius cuts 115, 125 contain a thread profile 135 that matches the thread profile of the fixation screw, thereby further increasing the stability of fixation.

Figure 1B:
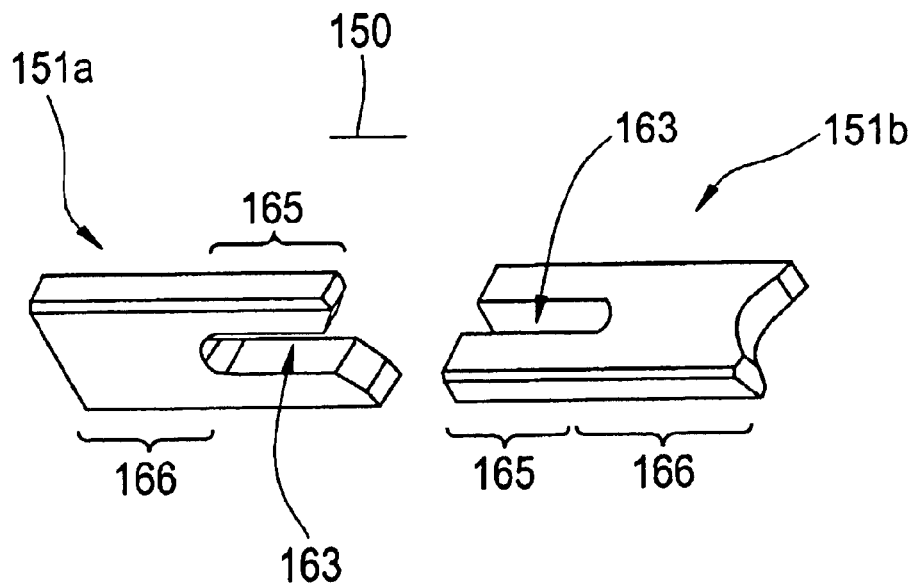
FIG. 1 shows diagrams depicting different shapes and constructions of an implant in accordance with the subject invention.
Figure 1C:
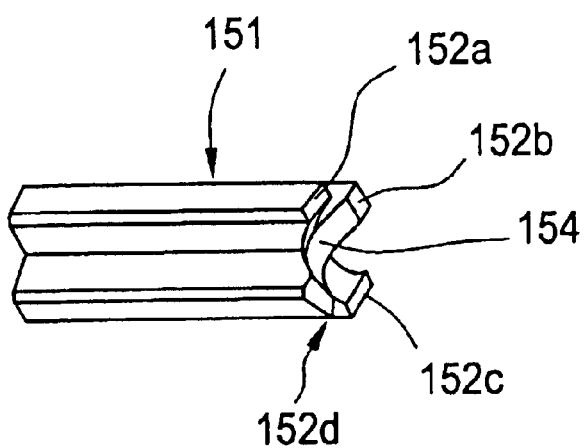

Referring to FIG. 1B–C, another embodiment directed to an implant 150 that employs a bone block, 151 that comprises a 'tee-' or 'cross-'shaped profile. The bone block is comprised of two interlocking substantially planar pieces, 151*a* and 151*b*, that comprise a slot 163 and slip together to present four fins, 152*a–d*, that radiate from a center point, 154. The substantially planar segments comprise a slot 163 that defines a slotted section 165 and a body section 166. The preferred length of the bone block, 151, is approximately 2.5 mm, and the preferred diameter may range from approximately 2.0 to 12.0 mm.

Figure 1D:
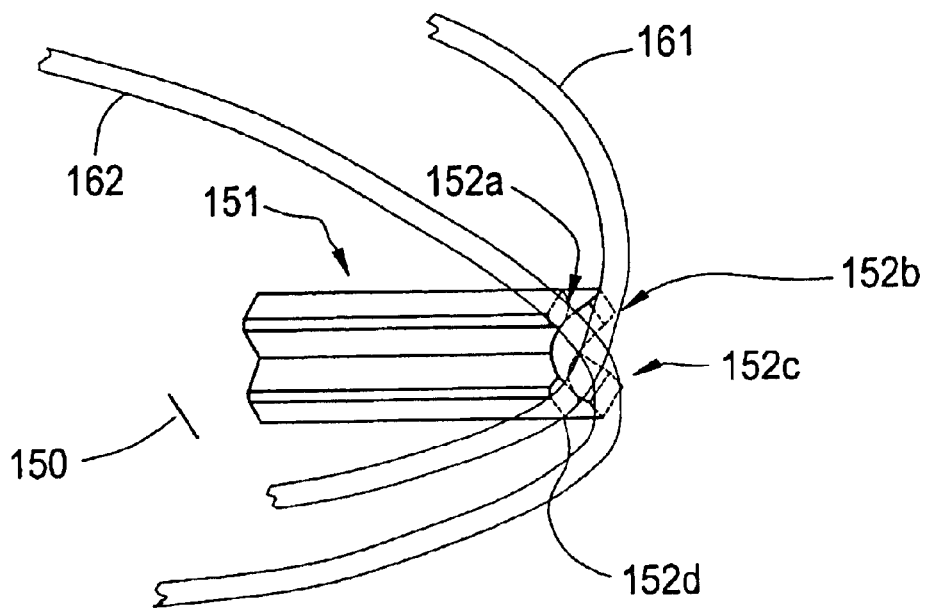
Figure 1E:
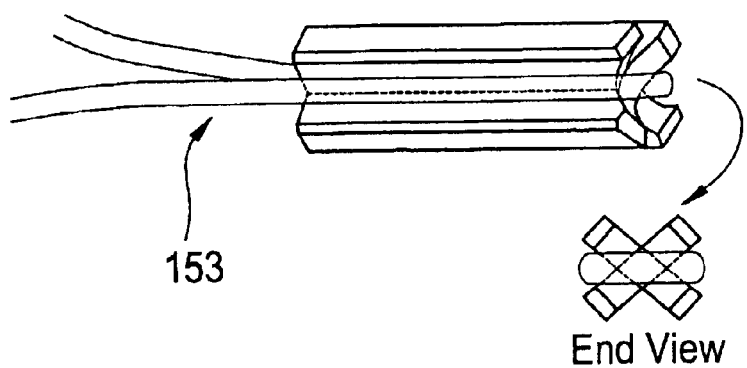

Processed soft tissue is attached to the bone blocks by various conventional means known to those skilled in the art, as described below. In addition, the processed soft tissue is attached by wrapping through holes made in the fins, 152*a–d*, of the bone block 151. As shown in FIG. 1D, the processed soft tissue 153 also can be passed into one channel and out a second channel and then fastened to form a loop (as by sutures, tying, etc.). In a preferred embodiment (shown in FIG. 1C), two separate flexible bands 161 and 162 (natural, e.g., dermis or synthetic) are looped over the top of the bone block 151, wherein one band 162 contacts fins 152*a*and *c*, and the second band 161 contacts fins 152*b* and *d*. When the bone block 151 is positioned into a channel, such as a tunnel formed in a patient's bone during surgery, the two bands looped over the bone block 151 are compressed against the fins 152*a–d* and thereby secured into place. Alternatively, the ends of the fins can comprise teeth or are otherwise irregular to further prevent slippage of the bands.

Figure 1F:
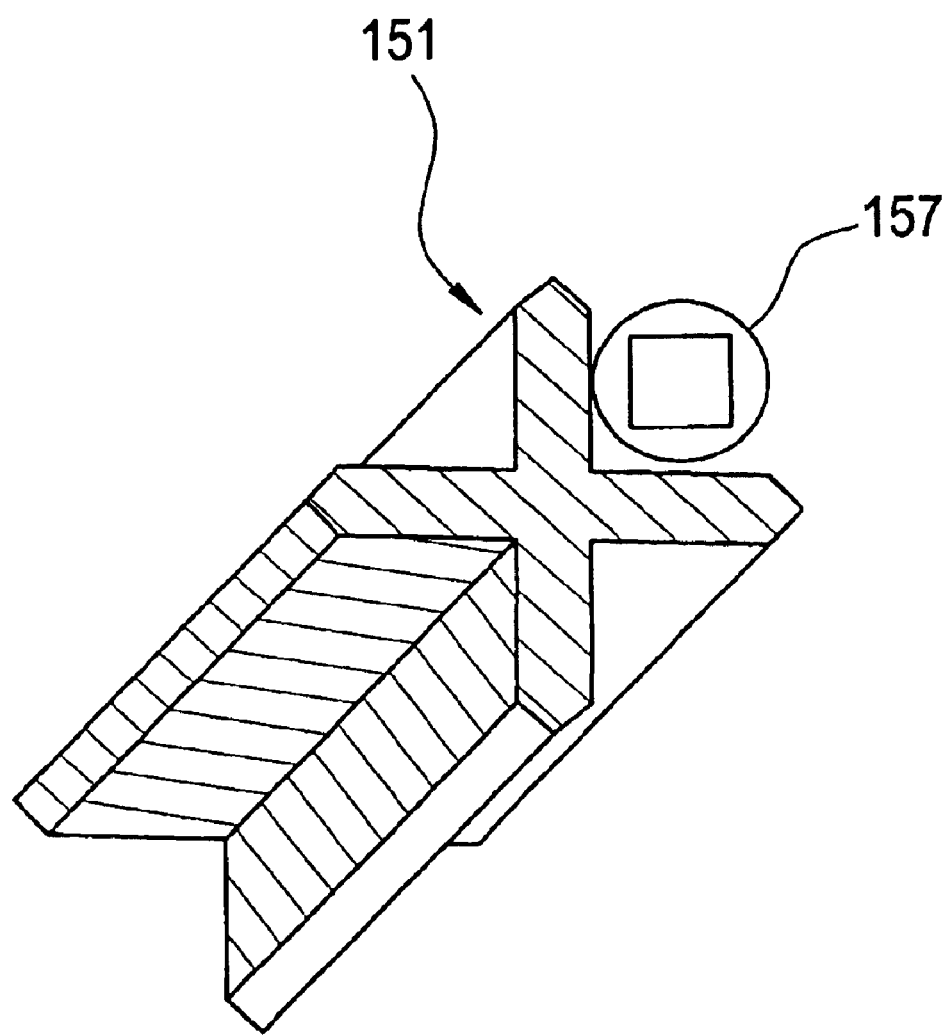

To fasten the tee-shaped bone block to the bone of a recipient in need of an implant, a round hole is drilled into the site of placement. The bone block is inserted to the desired depth, and at least one interference screw, 157 (FIG. 1F) is placed along side the bone block 151 and is tightened to set compress the bone block against the wall of the hole in the recipient's bone.

It is well recognized that many other shapes of bone blocks, as known or conceived by one of ordinary skill in the art, will serve the purpose of attachment in the present invention. For instance, a bone block with three, rather than four fins, in profile, can be used.

Figure 2A:
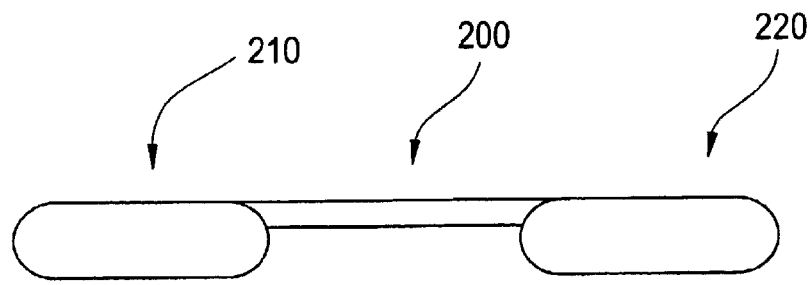

Referring now to FIG. 2, three different embodiments of the subject DDGs are shown. FIG. 2A shows an embodiment that comprises a basic configuration of the subject DDGs.

Figure 2B:
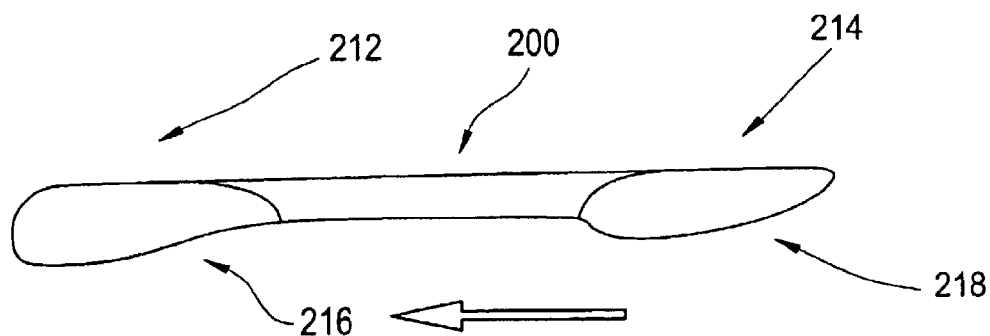
Figure 2C:
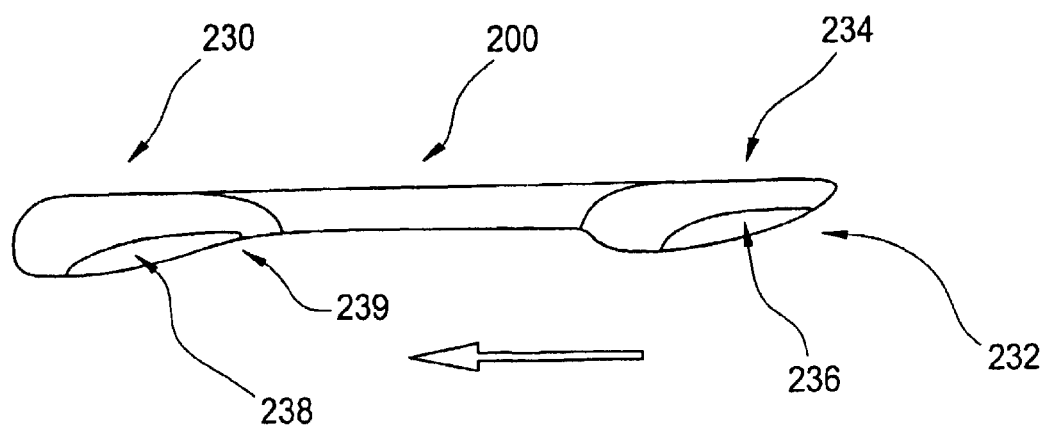

Bone blocks 210 and 220 are in a pre-shaped dowel form with no groove thereon, and are connected by processed dermis 100. FIG. 2B shows another version of the DDG, wherein the bone blocks are pre-shaped into dowels with tapered ends. Bone block 212 is a dowel that has a proximal tapered region 216 in relation to processed dermis 200, and bone block 214 is pre-shaped into a dowel that has a distal tapered region 218 in relation to processed dermis 200. FIG. 2C illustrates a preferred version of the invention, which has a bone block 230 with a proximal tapered region 239 and a groove 238 positioned on the bone block 230. This version also comprises a second bone block 234 with a distal tapered region and a groove 236 positioned on bone block 234 as well. The embodiments shown in FIGS. 2B–C are tapered such that implantation into a pre-formed tunnel in recipient bone is preferred to occur in the direction of the arrow.

In an alternative embodiment, the subject invention is directed to an implant having at least one bone block portion and at least one processed dermis section, wherein the bone block portion comprises a groove on its exterior. Once the bone blocks are extracted, they are machined into a dowel or other desired shape. In a specific embodiment, the dowel is machined into dimensions suitable for various surgical procedures. The machining is preferably conducted on a graduated die, a grinding wheel, a core cutter, a lathe, or machining tools that are specifically designed and adapted for this purpose. Preferred dimensions of the diameter for the dowels include 9 mm, 10 mm, 11 mm, and 12 mm. Reproducibility of the product dimensions is an important feature for the successful use of such grafts in the clinical setting.

The bone ends, whether in the shape of a dowel, other shapes described herein, or shapes known to those skilled in the art, are attached to the processed dermis by means such as chemical annealing, chemical adhesive, suturing (optionally through drilled holes in the bone), pinning to, or wrapping and tying the processed dermis around the bone ends (and optionally applying a suitable adhesive). When the attachment means includes use of tying the processed dermis to a bone end, the bone end optionally has grooves transverse to the long axis of the assembly which may receive the windings of the wrapping line (suture material or other suitable line). Furthermore, a block may be used that comprises an assembled block formed from two or more individual segments fastened together. The block made be made from cortical, cancellous bone segments, or both that are obtained from allogenic, autogenic, or xenogenic sources. The bone segments may be mineralized, or partially or fully demineralized. Furthermore, the block may be made from synthetic segments or a combination of bone and synthetic segments. Synthetic materials contemplated for use herein include, but are not limited to, stainless steel, titanium, cobalt chromium-molybdenum alloy, and a plastic of one or more members selected from the group consisting of nylon, polycarbonate, polypropylene, polyacetal, polyethylene oxide and its copolymers, polyvinylpyrolidone, polyacrylates, polyesters, polysulfone, polylactide, poly(L-lactide) (PLLA), poly(D,L-lactide) (PLA), poly(glycolide) (PGA), poly(L-lactide-co-D,L-Lactide) (PLLA/PLA), poly (L-lactide-co-glycolide) (PLA/PGA), poly(glocolide-co-trimethylene carbonate) (PGA/PTMC), polydioxanone (PDS), polycaprolactone (PCL), polyhydroxybutyrate (PHBT), poly(phosphazenes), poly(D,L-lactide-co-caprolactone) (PLA/PCL), poly(glycolide-co-caprolactone) (PGA/PCL), poly(phosphase ester), polyanhydrides, polyvinyl alcohol, hydrophilic polyurethanes, and a combination of one or more bioabsorbable polymers. Copending U.S. application Ser. No. 09/782,594 is incorporated herein by reference for disclosure on assembled implants.

Another shape of bone block is shown in FIG. 5. A two-part bone fixation plug, or screw, 501, has a first half, 502 and a second half, 503, that fit together. Each half, 502 and 503, has an outer surface, 520 and 521, respectively, that comprises approximately half of a generally conical shape. Each half, 502 and 503, has an inner mating surface, 522 and 523, respectively, whose surface generally matches the other side's inner mating surface so as to form, when joined together or in close proximity, a substantially conical surface on the outer surface. The shape of the inner mating surfaces may be curvilinear, flat, or a combination, or may comprise ridges, grooves, teeth or some other irregular shape to aid in gripping the soft tissue placed thereon. In a preferred embodiment the inner mating surfaces are substantially flat.

One or both of the inner mating surfaces 522 and 523 have one or more protrusions for alignment that, upon mating of the halves 502 and 503, enter matching voids or holes to align the joining together of the halves, 502 and 503. As shown in FIG. 5, the protrusions may be in the form of pins 524 from a first half, 502, that enter counterposed holes 525 in a second half, 503. The end section, 504, of a processed soft tissue, 505, such as dermis, is positioned between the inner mating surfaces, 522 and 523. The ends 530,531 of the plug, 501, preferably have driver hole formed therein to receive a driving tool when the two halves 502,503 are brought together; for instance, a shallow hexagonal cavity for a hex (Allen) wrench, a lateral or 'tee' slot for a screwdriver, the outer border shaped hexagonally to receive an open end wrench or socket, or other means known to those of ordinary skill in the art.

The plug, 501, has threads, 508, on the generally conical outer surfaces, 520 and 521. The threads of the first half, 502, and the second half, 503, of the plug, 501, are generally of the same size and are designed to approximately meet when the halves are joined together. When the halves, 502 and 503, are joined together, the plug, 501, is threaded into a sized hole in a bone of a recipient in need of an implant. As the plug passes farther into the hole, the inner mating surfaces, 522 and 523, are compressed closer together, and these compress against the soft tissue end, 504. This fastens the soft tissue, 505, to the bone block.

It is noted that various means to control the compression by and contact with the inner mating surfaces onto the soft tissue end, 504, can be effectuated. For instance, spacers or nub on the inner mating surfaces, preferably spaced peripherally to where the soft tissue end contacts, can stop the travel of the inner mating surfaces to provide a sufficient level of compression without crushing the soft tissue end, 504. Grooves or ridges on one or both of the inner mating surfaces, 522 and 523, can provide extra friction and pressure to avoid slippage. These can be alone or in combination with the peripheral spacers or nubs. Other designs can be implemented, where the basic goal is to compress a soft tissue graft component of the implant as the plug is being tightened into a hole, so the soft tissue component is attached to, or locked into the plug. For instance, the soft tissue end, 504, may have a thicker bitter end, and this may fit into a depression in one or both inner mating surfaces, so that upon compression this thicker end would be unable to slip through the narrower space between the rest of the flat surfaces. In another embodiment, the end, 504, of the soft tissue, 505, passes entirely through both inner mating surfaces of the plug, 501, so it extends beyond the ends, 530 and 531, of the plug, 501. The end of the implant material, 504, may be thickened so it abuts to the end surface 530, of the plug, 501, or it may be later adjusted and fastened, such as by suturing or tying in a knot.

Figure 5A:
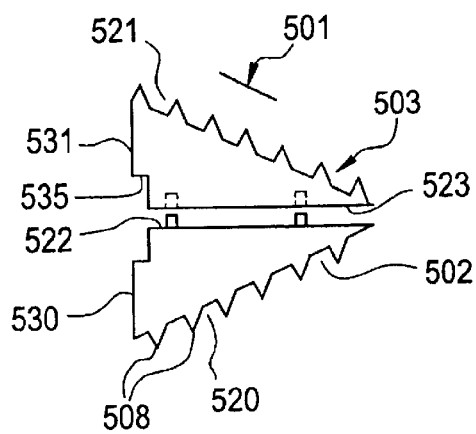
Figure 5B:
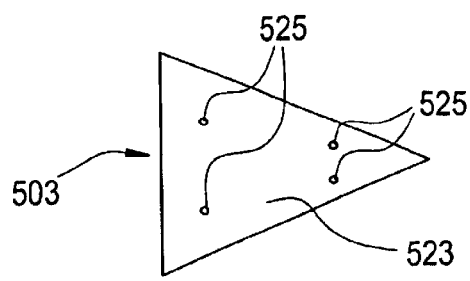
Figure 5C:
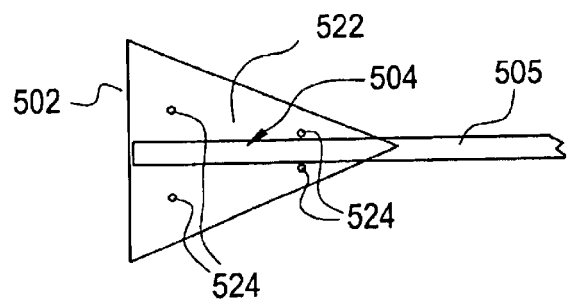
Figure 5D:
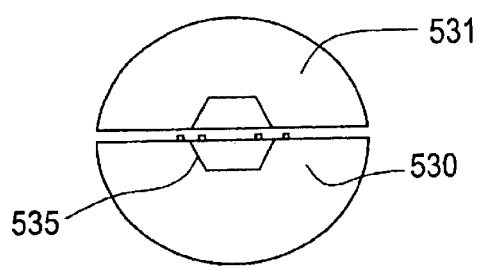
Figure 5E:
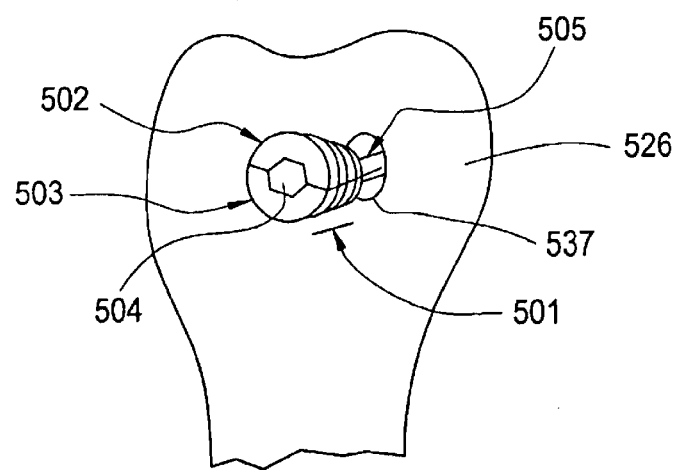

As shown in FIG. 5E, a variation of this embodiment is to insert the fixation plug, with the long portion of tissue 505 preceding the plug, into a hole 537 that passes entirely through a bone 526 of a recipient. A tapered hole may be used, so the soft tissue component passes from a hole that is relatively small in comparison to the opening into which the fixation plug is tightened. As the plug 501 comprising the two halves 502 and 503 is secured into the hole 537 they compress and secure the soft tissue 505.

The above discussion regards the joining of one end of a section of implant material, such as processed dermis, with a bone plug having various characteristics. It is recognized that when a bone-tendon-bone or similar implant is made, it typically has a bone plug at both ends of the flexible implant material that functions as a tendon matrix. A particular bone-tendon-bone or similar implant may use the same type of bone plug at both ends, or may use different types of bone plugs at each end, depending on the structural requirements of the recipient, the availability of implant parts, and other factors. Also, although the example in this section regarded processed dermis, it is recognized, as disclosed in the preceding section, that tissues other than dermis may be processed and used for bone-tendon-bone and similar implants.

Finally, as noted above, the bone that is used to construct bone blocks may be selected from cortical, cancellous, cortico-cancellous, or demineralized bone, obtained from human or xenograft sources. Optionally, synthetic material may be incorporated in combination with such bone. Also, bone blocks may be comprised of two or more segments assembled together in a assembled allograft implant.

IV. Implants for Augmenting or Replacing the Spinal Anterior Longitudinal Ligament (ALL) and Other Uses In another aspect of the invention, a processed dermis implant (DDG) is used to augment or replace the function of the anterior longitudinal ligament (ALL), such as after a surgery that partially or completely severs the ALL (such as during insertion of disc replacement implants or prostheses), or after other damage (e.g., trauma) to the ALL. Preferably, the DDG is calcified at the ends to allow use of stronger means of attachment. It is noted that, depending on the nature of the surgery, a disc replacement/spinal fusion operation may access the vertebrae by partially or completely severing the ALL. Without a fully functional ALL, there is a risk of damage to the spine from excessive backward bending in that the intact ALL tensions the anterior span of the spine. Also, the DDG stabilizes the motion of the segment anteriorly. This is more conducive to spinal fusion.

An additional advantage of a DDG produced according to the method of this invention, for the application of augmenting or replacing a partially or completely severed ALL, is that is may block and thereby prevent the expulsion of interbody grafts. Such DDGs are preferably affixed to the vertebral bodies with screws, pins, staples or anchors of various types known in the art or heretofore developed. The attachment means preferably are well secured and with means to minimize the possibility that the attachment means will loosen, as such loosening in the vertebral area, rich with blood vessels and nerves, can be extremely dangerous and potentially leads to death. One embodiment uses bone screws which are applied with a bone paste to accelerate bone growth onto the bone screws.

As a result of placing a DDG to span two adjacent vertebrae, lumber extension is reduced, thereby providing a more stable environment to promote fusion. In FIG. 3, there is provided one embodiment 300 of the DDG ALL implant according to this invention. This implant 300 is prepared from processed dermis which has been folded to provide sufficient strength. A top portion, 310, and a bottom portion, 320, are prefereably fully mineralized, or partially mineralized, as by calcification. Also, the mineralization may be restricted to the surface layer(s) to modify the stress-fracture behavior of the implant. The top portion 310 and the bottom portion 320 each have a series of holes 305 by means of which the DDG implant is affixed to a superior vertebra V1 and an inferior vertebra V2. The intermediate section, 330, is processed to maintain a desired degree of flexibility while maintaining sufficient tensional strength. In this fashion, while permitting a slight amount of motion, the DDG implant substantially restricts motion at the vertebral segment spanned by the DDG implant. Also shown in outline is a pair of interbody implants 340 inserted between superior vertebra V1 and inferior vertebra V2. In FIG. 3B, there is shown a further embodiment of the DDG implant of this invention which is identical in all respects to the implant shown in FIG. 3A, but wherein this embodiment has an enlarged upper segment 310' and lower segment 320' for affixation to the vertebrae V1 and V2. It will be appreciated that the precise shape of the DDG implant is not critical. Furthermore, the DDG implant may span more than two vertebrae. In one preferred embodiment the DDG implant is 20 to 30 mm wide and 3 mm thick, and has one aperture in each of its four comers.

In yet a further embodiment of the DDG implant of this invention, there is provided a spinal tension band, STB. Typically, in spinal fusions, the motion segment adjacent to the fused segment (the juxtaposed discs) have been found to rapidly degrade. This degradation appears to be due to the hyper motion at these levels, due to the decreased motion at the fused segments. The STB of this invention assists in preventing this degradation and can avoid the need for further surgery, by spanning the fused segments and attaching to the juxtaposed vertebral body at the spinous process thereof. The STB may be used in any region of the spine, but is typically most useful for spanning fusions at two, three, or more levels. The STB of this invention replaces or augments use of flexible stainless steel, titanium cables, elastomeric or polymeric synthetic materials currently in use. Accordingly, known techniques for attaching such devices to the spinous processes may be used, or the STB may be affixed to juxtaposed vertebral bodies in a fashion analogous to that described above for the DDG implant to augment or replace the ALL function.

In FIG. 4, there is disclosed one embodiment of the STB 400 of this invention. As can be seen, the STB 400 is affixed to a superior vertebra, VA, and an inferior vertebra, VB, each of which are juxtaposed to a vertebra V1 and V2, which are being fused to each other by means of interbody fusion devices IB1 and IB2. Intermediate portion 410 is dermis processed to maintain a desired level of flexibility and strength, while the top portion 420 and the bottom portion 430 are preferably in a mineralized or partially demineralized state. Affixation means 425 and 435 are provided for fixation of the STB to the juxtaposed vertebrae VA and VB, respectively. Those skilled in the art will appreciate that this embodiment of the invention may be applied to any other anatomical structure to minimize motion of such structures in relation to each other. For example, the tension band of this invention may be utilized outside of the spinal context, for example for the repair of a split sternum in a sternotomy. Also, the tension band of this invention is used for spanning a bone fracture site. In this application, one or more tension bands are attached to attachment sites on both sides of the fracture.

It is further appreciated that other implant substances may be processed and utilized for an implant to augment or replace an ALL or as an STB or other tension band. Among the implant materials that may be used are: segmentally demineralized bone; fascia, pericardium; ligaments; tendons (including as processed as described above, herein); ligaments; muscle; dura; xenograft demineralized bone; xenograft segmentally demineralized bone; calcified implant materials made from soft tissue, fascia, pericardium, UBM, SIS, or woven soft tissue (skeletal muscle); or any combination of these implant substances, and optionally in combination with biocompatible synthetic materials. Further, as appropriate these may be attached to bone pieces (human or xenograft), for instance when the bone pieces provide a preferred means of affixation to the bone or other part of the recipient.

It also is noted that strip size variations are recognized and are within the scope of this invention. For instance, wide or narrow strips comprising the ALL, STB, or tension band implants may be used. Also, strips each comprising a layering of dermis, or other allograft tissues such as those listed above, may be used at one or two levels (e.g., one internal to the other), and the implants may be used for the cervical, thoracic, or lumbar regions of the spine. Further, the implants described in this invention may be used to augment or replace the posterior longitudinal ligament for procedures where this ligament is in need of augmenting or replacing.

Those skilled in the art will appreciate that the graft may be an autograft, allograft, or xenograft. Xenograft implants may further require treatments to minimize the level of antigenic agents and/or potentially pathogenic agents present in the graft. Techniques now known, or those which are later developed, for preparing tissue such that it is suitable for and not rejected by the recipient are incorporated herein. In cases where the graft is an allograft, a donor is preferably screened for a wide variety of communicable diseases and pathogens, including human immunodeficiency virus, cytomegalovirus hepatitis B, hepatitis C and several other pathogens. These tests may be conducted by any of a number of means conventional in the art, including, but not limited to, ELISA assays, PCR assays, or hemagglutination. Such testing follows the requirements of the following associations: (a) American Association of Tissue Banks. Technical Manual for Tissue Banking, Technical Manual-Musculoskeletal Tissues, pages M19–M20; (b) The Food and Drug Administration, Interim Rule, Federal Register, Vol. 58, No. 238, Tuesday, December 14, Rules and Regulations, 65517, D. Infectious Disease Testing and Donor Screening; (c) MMWR, Vol. 43, No. RR-8, Guidelines for Preventing Transmission of Human Immunodeficiency Virus Through Transplantation of Human Tissue and Organs, pages 4–7; (d) Florida Administrative Weekly, Vol. 10, No. 34, Aug. 21, 1992, 59A-1.001-014, 59A-1.005(12) (c), F.A.C., (12)(a)–(h), 59A-1.005(15, F.A.C., (4) (a)–(8). In addition to a battery of standard biochemical assays, the donor, or their next of kin can be interviewed to ascertain whether the donor engaged in any of a number of high risk behaviors such as having multiple sexual partners, suffering from hemophilia, engaging in intravenous drug use etc. Once a donor has been ascertained to be acceptable, the tissue for obtaining the DDGs as described above are recovered and cleaned.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An implant useful in orthopedic surgery comprising at least one assembled bone block and at least one section of flexible material attached to said at least one assembled bone block, wherein said at least one assembled bone block comprises a first substantially planar segment of cortical bone having a first slotted section thereon and a second substantially planar segment of cortical bone having a second slotted section thereon, wherein said first substantially planar segment and said second substantially planar segment are fastened together by sliding the first slotted section into a slot formed by the second slotted section.

2. The implant of claim 1, wherein said first segment of cortical bone is demineralized.

3. The implant of claim 1, wherein said at least one section of flexible material is selected from the group consisting of ligament, tendon, muscle, dura, pericardium, fascia, peritoneum and demineralized bone.

4. A bone-ended graft useful in orthopedic surgery comprising at least one assembled bone block and at least one section of flexible tissue attached to said at least one assembled bone block, wherein said at least one assembled bone block comprises a first substantially planar segment of allograft or xenograft cortical bone having a first slotted section and a body section thereon and a second substantially planar segment of allograft or xenograft cortical bone having a second slotted segment thereon, said first and second substantially planar section and body section comprise a slot longitudinally defined thereon such that said first and second substantially planar segments section and a body section, and wherein said first and second are fastened together by sliding the first slotted section into the slot of the second slotted section.

5. The bone-ended graft of claim 4, wherein said flexible tissue comprises soft tissue, dermis, pericardium, fascia, woven soft tissue, urinary bladder membrane, dura mater, demineralized bone, or skeletal muscle.

6. The bone-ended graft of claim 1, wherein said flexible tissue is dermis.

7. The bone-ended graft of claim 4, wherein said at least one assembled bone block comprises two or more longitudinal fins, and wherein said flexible tissue is attached to said assembled bone block by contact with at least one of said two or more fins.

8. The bone-ended graft of claim 4, wherein said at least one assembled bone block is cut to provide a groove sufficient to accommodate a fixation screw.

9. The bone-ended graft of claim 8, wherein said groove is a radius cut extending the length of the assembled bone block.

10. The bone-ended graft of claim 4, wherein said at least one assembled bone block is shaped into a dowel.

11. The bone-ended graft of claim 4, wherein said at least one assembled bone block is 9 mm, 10 mm, 11 mm, or 12 mm in diameter.

12. The bone-ended graft of claim 4, wherein said groove has a thread profile positioned on its surface.

13. The bone-ended graft of claim 4, wherein said flexible tissue has a first end and a second end, and wherein said one or more bone blocks comprise a first assembled bone block attached to said first end and second assembled bone block attached to said second end.

14. The bone-ended graft of claim 4 wherein said implant material is attached to said at least one assembled bone block by chemical annealing, chemical adhesive, suturing, pinning to, or wrapping and tying the implant material around the bone ends and optionally applying a suitable adhesive.

15. The bone-ended graft of claim 4 wherein at least one of said at least one assembled bone block comprises two or more longitudinal fins extending from at least one end of said at least one assembled bone block.

16. The bone-ended graft of claim 15 wherein the processed implant material passes through at least one hole in at least one fin of the bone-ended graft, and attaches to a section of itself to form a loop encircling the bone-ended graft.

17. The bone-ended graft of claim 15 wherein aid at least one section of material contacts the ends of two or more fins and is secured into place by compression onto said two or more fins.

18. The bone-ended graft of claim 15, wherein said at least one section of flexible tissue passes along a first channel between adjacent fins, loops around a far end of the bone-ended graft, and passes back along a second channel between adjacent fins, and attaches to a section of itself to form a loop encircling the bone-ended graft.

19. The bone-ended graft according to claim 4 further comprising at least one interference screw that is placed alongside said at least one bone-block, wherein when so placed in a hole in a bone in a recipient in need of said bone-ended graft, said screw compresses against an adjacent section of a wall of said hole, and also compresses said bone-ended graft against an opposite wall of said hole.

20. An assembled implant, comprising:
  a. a first matable segment having a first inner mating surface, said first inner mating surface comprising at least one protrusion extending therefrom;
  b. a second matable segment having a second inner mating surface, said second inner mating surface comprising at least one hole formed thereon to receive the at least one protrusion on said first inner mating surface; and c. a length of flexible material comprising processed soft tissue and having a first end and a second end, said first end placed between the inner mating surfaces of the first and the second segments, such that when the first and second segments are joined so the at least one hole receives the at least one protrusion, said first end of said length of flexible material is compressed or held therebetween and said second end extends beyond said matable segments,
  wherein said first matable segment and said second matable segment are semi-conical shaped and comprise an exterior surface with threads defined thereon, wherein when said first and second segments are brought together, said threads are aligned.

21. The assembled implant of claim 20, wherein the first inner mating surface and the second inner mating surface are substantially flat.

22. The assembled implant of claim 20, wherein said at feast one protrusion comprises a pin.

23. The assembled implant of claim 20, wherein said inner mating surface of said first segment, second segment or both comprises, teeth, ridges, grooves or another irregular shape to prevent slippage of said flexible material out of said assemblable fixation plug when assembled.

24. The assembled implant of claim 23, additionally comprising an aperture formed on at least one end to receive a driving tool.

25. The assembled implant of claim 20, additionally comprising a depression in one or both of the inner mating surfaces, and a thickened section of flexible material positioned in said depression, whereby upon tightening of the first and second segments, the thickened section is retained in said depression and is restricted from sliding out of the assembled implant.

26. The assembled implant of claim 20, wherein said first matable segment and said second matable segment are comprised of allograft or xenograft mineralized bone, demineralized bone or a combination thereof; and said length of flexible material is comprised of soft tissue selected from the group consisting of ligament, tendon, muscle, dura, pericardium, fascia, peritoneum and demineralized bone.

27. A dermis derived bone-ended graft useful in orthopedic surgery comprising at least one assembled bone block and at least one section of flexible material attached to said at least one assembled bone block, wherein said at least one assembled bone block comprises a first substantially planar segment having a first slotted section thereon and a second substantially planar segment having a second slotted section thereon, wherein said first substantially planar segment and said second substantially planar segment are fastened together by sliding the first slotted section into a slot formed by the second slotted section, and wherein said at least one section of flexible material is an elongated section of processed dermis.

28. The graft of claim 27, wherein at least one of the at least one assembled bone block is comprised of cortical, cancellous, cortico-cancellous, or demineralized bone, obtained from human or xenograft sources, optionally in combination with the synthetic material.

29. The graft of claim 28, wherein at least one of the at least one assembled bone block is comprised of two segments.

* * * * *